(12) United States Patent
Shalaby

(10) Patent No.: US 9,370,574 B2
(45) Date of Patent: *Jun. 21, 2016

(54) COMPOSITE ABSORBABLE/BIODEGRADABLE RINGS FOR CONTROLLED DRUG DELIVERY

(71) Applicant: Poly-Med, Inc., Anderson, SC (US)

(72) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/669,105

(22) Filed: Mar. 26, 2015

(65) Prior Publication Data

US 2015/0196647 A1     Jul. 16, 2015

Related U.S. Application Data

(63) Continuation of application No. 13/771,201, filed on Feb. 20, 2013, now Pat. No. 8,992,968, which is a continuation of application No. 10/860,677, filed on Jun. 3, 2004, now Pat. No. 8,404,272.

(60) Provisional application No. 60/482,898, filed on Jun. 26, 2003.

(51) Int. Cl.
| | |
|---|---|
| *A61F 6/14* | (2006.01) |
| *A61F 13/00* | (2006.01) |
| *A61K 47/34* | (2006.01) |
| *A61L 31/12* | (2006.01) |
| *A61L 31/16* | (2006.01) |
| *A61K 47/10* | (2006.01) |
| *A61K 47/32* | (2006.01) |

(52) U.S. Cl.
CPC ............... *A61K 47/34* (2013.01); *A61K 47/10* (2013.01); *A61K 47/32* (2013.01); *A61L 31/129* (2013.01); *A61L 31/16* (2013.01); *A61L 2300/602* (2013.01)

(58) Field of Classification Search
None
See application file for complete search history.

(56) References Cited

U.S. PATENT DOCUMENTS

| | | |
|---|---|---|
| 3,545,439 A | 12/1970 | Duncan |
| 3,920,805 A | 11/1975 | Roseman |
| 4,629,449 A | 12/1986 | Wong |
| 4,795,761 A | 1/1989 | Curtis-Prior et al. |
| 4,983,393 A | 1/1991 | Cohen et al. |
| 5,069,906 A | 12/1991 | Cohen et al. |
| 5,176,907 A | 1/1993 | Leong |
| 5,192,330 A | 3/1993 | Chang et al. |
| 5,211,952 A | 5/1993 | Spicer et al. |
| 6,083,916 A | 7/2000 | Nonomura et al. |
| 6,086,909 A | 7/2000 | Harrison et al. |
| 6,103,256 A | 8/2000 | Nabahi |
| 6,127,327 A | 10/2000 | Camenzind et al. |
| 6,159,240 A | 12/2000 | Sparer et al. |
| 6,299,894 B1 | 10/2001 | Markkula et al. |
| 6,309,669 B1 | 10/2001 | Setterstrom et al. |
| 6,416,779 B1 | 7/2002 | D'Augustine et al. |
| 6,416,780 B1 | 7/2002 | Passmore et al. |
| 6,503,528 B1 | 1/2003 | Bieniarz et al. |
| 6,572,874 B1 | 6/2003 | Pauletti et al. |
| 6,591,654 B2 | 7/2003 | Kwok |
| 7,416,559 B2 | 8/2008 | Shalaby |
| 7,521,064 B2 | 4/2009 | Saxena et al. |
| 8,062,658 B2 | 11/2011 | Shalaby et al. |
| 8,399,013 B2 | 3/2013 | Shalaby |
| 8,404,272 B2 | 3/2013 | Shalaby |
| 2003/0059456 A1 | 3/2003 | Malcolm et al. |
| 2004/0077601 A1 | 4/2004 | Adams et al. |
| 2004/0260386 A1 | 12/2004 | Shalaby |
| 2005/0175665 A1 | 8/2005 | Hunter et al. |
| 2006/0240071 A1 | 10/2006 | Lerner et al. |
| 2009/0291925 A1 | 11/2009 | Shalaby |

FOREIGN PATENT DOCUMENTS

| | | |
|---|---|---|
| EP | 0891783 | 1/1999 |
| EP | 1827328 | 8/2011 |
| WO | WO 00/59559 | 10/2000 |
| WO | WO 02/015832 | 8/2001 |
| WO | WO 2006010097 | 1/2006 |
| WO | WO 2006028475 | 3/2006 |

OTHER PUBLICATIONS

McCullough & Shalaby, Tailored Polymeric Materials for Controlled Delivery Systems, ACS Symposium Series vol. 709 (1998), chapter 2.
Cowsar et al. "Biodegradable and Non-biodegradable Fibrous Delivery Systems" International Workshop on Long-Acting Contraceptive Delivery Systems; pp. 145-163 (1984).
Woolfson, a.D. et al. Int. J. Pharm. 2006, vol. 325, pp. 82-89.
Malcolm, R.K. et al. J. Antimicrobial Chemotherapy, 2005, vol. 56, pp. 954-856.
Garlotta, Donald; Journal of Polymers and the Environment, vol. 9, No. 2, Apr. 2001.

*Primary Examiner* — Jeffrey T Palenik

(57) ABSTRACT

A fiber-reinforced composite ring for the controlled release of at least one bioactive agent includes a biocompatible matrix reinforced with absorbable/biodegradable fibers capable of providing the mechanical properties needed for inserting and maintaining the ring in a body cavity for a desired period of time. Such ring system as can be used for the intravaginal, intraperitoneal, and subcutaneous delivery of at least one bioactive agent, including those used as contraceptives, antimicrobial agents, and/or antiviral agents, as well as those for the treatment of cancer.

36 Claims, No Drawings

COMPOSITE ABSORBABLE/BIODEGRADABLE RINGS FOR CONTROLLED DRUG DELIVERY

CROSS-REFERENCE TO RELATED APPLICATIONS

This application is a continuation of U.S. application Ser. No. 13/771,201, filed Feb. 20, 2013, now U.S. Pat. No. 8,992, 968. U.S. application Ser. No. 13/771,201 is a Continuation of U.S. application Ser. No. 10/860,677, filed Mar. 6, 2004, which issued as U.S. Pat. No. 8,404,272 on Mar. 26, 2013. U.S. application Ser. No. 10/860,677 claims priority to U.S. Provisional Application No. 60/482,898, filed Jun. 26, 2003, all of which are hereby incorporated by reference in their entirety.

FIELD OF THE INVENTION

This invention deals with a fiber-reinforced composite ring system for the controlled release of one or more bioactive agent(s) at the desired biological sites, which may entail intravaginal, intraperitoneal, and subcutaneous administration of such agent(s). The composite ring system is designed to modulate the bioactive agent(s) release profile as well as the mechanical property of the ring, in part or totally through the controlled degradation of the absorbable components of the composite system.

BACKGROUND OF THE INVENTION

The subject of drug delivery in general was reviewed by McCulloch and Shalaby [Tailored Polymeric Materials for Controlled Delivery Systems, ACS Symposium Series, Vol. 709 (1998)]. Part of this review pertained to the specific subject of intravaginal delivery which was discussed in a separate chapter (Chapter 2), and excerpts therefrom are included in the background information on the clinical effectiveness and attributes of intravaginal drug delivery noted below.

In recent years, a variety of women's health issues have generated considerable interest. Areas of particular importance have included obstetrics, medical terminations, contraception, infertility, sexually transmitted infections, and cancers of the reproductive tract. In the postmenopausal female, the reduction of endogenous estrogen has been shown to profoundly influence the skeletal and lower urogenital systems. Concurrently, a number of therapeutic strategies have been developed to improve treatment in these respective areas. While oral, intravenous, and transdermal routes of drug administration have been widely utilized, intravaginal drug delivery has been studied to a far lesser extent. Interestingly, there are many instances where intravaginal drug delivery may by ideal. For example, it is postulated that drug specificity for the reproductive tract may be more effectively achieved through intravaginal administration. Thus, elevated levels may be attained at a fraction of the oral or parenteral doses. A secondary benefit would be to improve patient compliance in terms of dosing frequency and/or systemic side effects. The rich vascular supply of the vagina also represents a rapid portal of entry when systemic drug levels are desired. Because of the anatomy, first-pass hepatic metabolism is bypassed which could be utilized to improve the relative bioavailability of certain agents.

Intravaginal drug delivery can be utilized for topical, local, or systemic effects. Topical administration has been used in the treatment of bacterial or fungal infections, atrophic vaginitis, and vaginal intraepithelial neoplasia. In terms of local therapy, vaginal drug administration has been used to treat stress urinary incontinence, labor induction, medical abortions, and infertility. The advantage of this route is the large surface area for drug absorption and ease of administration.

Current trends in intravaginal drug delivery are outlined below and include (1) labor induction; (2) hormone replacement therapy; (3) contraception; (4) infertility; (5) infectious diseases; and (6) gynecologic oncology.

Labor Induction—Spontaneous labor and delivery involve a sequence of events that include softening, or ripening, and effacement of the cervix. Labor induction is indicated when there is evidence of preeclampsia, diabetes, heart disease, or fetal-placental insufficiency. Prolonged labor in the context of an unfavorable cervix can increase the likelihood of numerous maternal and fetal complications such as infection, fetal distress/demise, the need for operative delivery, and postpartum hemorrhage. Pharmacological intervention is often implemented in an effort to "ripen" the cervix to facilitate vaginal delivery. Numerous studies dating back to the 1970's have documented the successful use of prostaglandins for labor induction through intracervical or intravaginal routes of administration. In recent years, dinoprostone (a synthetic prostaglandin E2) has been used for cervical ripening via vaginal administration. Early efforts utilized glycerol ester based formulations to deliver dinoprostone. Currently methylcellulose based materials and polyethylene oxide based hydrogels have been formulated for cervical ripening. Early concerns for these devices were related to dose dumping and ease of removal. While a burst release of drug in the early phase is difficult to avoid, signs and symptoms of toxicity have been less significant with current devices. The success of this system has largely been due to incorporating drug into hydrogel delivery systems where release is swelling-controlled and more predictable. In terms of retrieval, Cervidil® (a polyethylene oxide/urethane based hydrogel) is incorporated within a polyester net that can be used to remove the device should signs or symptoms of hyperstimulation result. It is thus expected that future delivery systems for labor induction will utilize both newer agents and/or polymeric systems. Although considerable interest has been placed on labor induction, it bears mention that other areas in obstetrics may benefit from intravaginal therapeutics. This includes the management of preterm labor with intravaginal tocolytic agents or through administration of antibiotics in the context of preterm rupture of membranes to prolong intrauterine gestational time. Labor augmentation in the latent period of stage I may be another phase of labor that could benefit from intravaginal therapeutics.

Hormone Replacement Therapy—Postmenopausal hormone replacement therapy (HRT) has received considerable attention in recent years. The dramatic shift away from their use in primary and secondary prevention for osteoporosis and increased risk in cardiovascular and hematologic events risk has been attributed to combination estrogen and progesterone therapy. However, estrogen-only therapy is still used for the treatment of vaginal and urogenital atrophy, and symptomatic relief of hot-flushes. Hormone replacement therapy can be achieved by many routes of administration. The most common of which are oral and transdermal administration. Vaginal estrogen creams have been in existence for many years. While systemic levels are achieved, daily administrations combined with patient compliance issues make this a less desirable approach to estrogen replacement. In response, vaginal estrogen-releasing rings have been developed to provide sustained drug release in a manner similar to transdermal delivery. Early investigators dispersed estradiol homogeneously into polysiloxane vaginal rings for this purpose. These delivery systems were capable of maintaining estradiol levels ranging from 109 pg/ml to 159 pg/ml for 3 months in postmenopausal volunteers. Serum levels could also be adjusted based on the loading dose of estradiol and surface area of the device. Estring® and other similar devices were later designed with an inner core or reservoir of estradiol and an outer polysiloxane sheath for diffusion-controlled release; and stable serum levels have been achieved for up to 3 months for the treatment of vaginal and urogenital atrophy.

Contraception—The development of new hormonal contraceptive modalities has been an ongoing effort for over forty years. Oral, injectable, and implantable contraceptives have all been widely used with exceptional efficacy. Intravaginal hormonal contraception was initially investigated using medroxyprogesterone. Medroxyprogesterone was homogeneously dispersed in cylindrical rings prepared from polysiloxane. Over a 28-day cycle, an absence of the midcycle luteinizing hormone (LH) surge was observed. Endometrial biopsies taken were found to be consistent with progestational effects. Furthermore, removal of the device resulted in prompt withdrawal bleeding. Similar designs have also been developed for 90-day clinical trials. Testing of a core designed vaginal ring containing norethindrone acetate and ethinyl estradiol revealed that ovulation and breakthrough bleeding were better controlled with average daily ethinyl estradiol release rates ranging from 30 to 65 mcg. However, unacceptably high levels of nausea resulted with the 65 mcg-daily release rates. Similar rings containing levonorgestrel have also been studied. Unlike the preceding ethinyl estradiol vaginal rings, there was greater individual variation in levonorgestrel levels, incomplete suppression of ovulation, and breakthrough bleeding.

Currently, intravaginal barrier and intrauterine contraceptive devices, with or without hormones, are available to inhibit ovulation and to prevent sperm migration into the cervix and fertilization. A literature search for non-hormonal, non-toxic and non-invasive contraceptive agents as well as the antimicrobial and antiviral agents revealed that metal ions and their derivatives, such as calcium chloride, sodium chloride, magnesium chloride, copper, and ferrous sulfate act as spermicidal and/or spermiostatic agents. Copper sulfate has been used in IUDs as a spermicidal agent. It is known that sulfhydryl groups are essential components of certain vital enzymes for stability of the sperm. The copper-based agents are toxic due to their sulfhydryl binding properties, and thus cause a direct deleterious effect on sperms. Copper also influences midcycle human cervical mucus by causing lysis of the mucus material, changing the physicochemical properties of the mucus resulting in a decrease in sperm penetration.

The medical management of abortions and ectopic pregnancies are two areas of converging study. Recent randomized trials utilized oral or intramuscular methotrexate with intravaginal administration of misoprostol to provide safe and efficacious medical abortions. These studies suggest that oral administration of methotrexate may have improved efficacy while minimizing systemic side effects. It is conceivable that intravaginal methotrexate administration may provide additional advantages in terms of higher local drug levels at lower doses. This could conceivably improve efficacy while further minimizing systemic side effects. Similarly, the medical management of ectopic pregnancies requires the intramuscular administration of methotrexate over 1 to 4 doses followed by leucovorin rescue. In this regard, the administration of an intravaginal methotrexate delivery system may be capable of releasing lower doses of drug over a predictable time course to improve efficacy and compliance while decreasing systemic side effects.

Infertility—Progesterone supplementation or replacement is widely implemented for assisted reproductive technology in the treatment of infertility. Oral administration of progesterone leads to extensive intestinal and hepatic metabolism. The standard of treatment for progesterone deficiency is through intramuscular administration which can be painful. Recently, an intravaginal progesterone gel (Crinone®) has been developed. The delivery system is a bioadhesive gel formulation prepared from polycarbophil. The gel is administered once or twice daily delivering 90 mg of micronized progesterone with each dose. Treatment may be continued for up to 12 weeks until placental autonomy is achieved. The manufacturers (Wyeth-Ayerst Laboratories) purport less drowsiness as compared to the oral form. This delivery system is also being studied in conjunction with oral estrogen for hormone replacement therapy.

Infectious Diseases—Interest in the administration of intravaginal agents for the treatment and prophylaxis of sexually-transmitted diseases and other infections has been considerable. Early efforts in this field had focused on treatment modalities for bacterial vaginosis. Bacterial vaginosis is a syndrome in women of reproductive age where the normal *Lactobacillus*-dominated vaginal microflora is replaced by high concentrations of mixed anaerobic and facultative flora. Typically, this includes *Peptostreptococcus* sp., *Gardnerella vaginalis, Mycoplasma hominis*, and *Ureaplasma urealyticum*. It is considered to be the most common vaginal infection and has been associated with an increased risk of preterm labor and delivery, premature rupture of membranes, chorioamnionitis, and pelvic inflammatory disease. Topical administration of clindamycin or metronidazole has been most successful in the treatment of bacterial vaginosis. Studies on the efficacy of 0.1% to 2.0% clindamycin creams administered daily for seven days in non-pregnant women indicated that the 2% cream had the greatest effect on bacterial vaginosis-associated flora with a 94% resolution of bacterial vaginosis both one week and one month after treatment. Similar findings have been reported elsewhere. The efficacy of intravaginal clindamycin has also been shown to be similar to oral metronidazole. The bioavailability of clindamycin has been shown to be minimal ranging from 2.7% to 4.7%. Intravaginal metronidazole has been studied to improve patient compliance and decrease side systemic side effects as seen with the oral regimen. Administration of intravaginal sponges containing either 250 mg (twice-daily for two days) or one gram (once-daily for three days) of metronidazole to a small group of women led to a cure rate of 85% after one week. Failure rates after one month were 42% in the low dose and 12% in the high dose group. Systemic side effects such as nausea, headache and metallic taste were slightly more frequent in patients using the higher dose sponge. In another study, the efficacy of 5 gm metronidazole gels (0.75%) administered twice-daily for 5 days. A clinical cure rate of 87% was observed after 9 to 21 days with a recurrence rate of 15% after one month. Furthermore, there were no significant side effects noted in the treatment group.

Current standards in the treatment of sexually transmitted diseases have focused on oral and intravenous administration of antibiotics and antiviral agents. While little has been done in terms of intravaginal treatment strategies, a growing interest in prophylaxis has emerged using vaginal microbiocides and antiviral agents. The ultimate goal is to develop a vaginal delivery system that has activity against a broad spectrum of pathogens, including human immunodeficiency virus (HIV).

A number of compounds have been considered such as benzalkonium chloride, chlorhexidine, nonoxynol-9, and polymixin B. In terms of HIV transmission, both virucidal agents and biomaterials that prevent HIV adsorption/fusion are being studied. Although this area is still in its infancy, the growing urgency for prevention strategies will quickly attract many investigators from multidisciplinary backgrounds to study this problem. It is clear, however, that the active agent as well as the delivery system will play an equal role in optimizing efficacy.

Vaginitis Due to Vaginal Infection:

Bacterial Vaginosis (BV) is the most common cause of vaginitis symptoms among women of childbearing age. Previously called non-specific vaginitis or *Gardnerella*-associated vaginitis. BV is associated with sexual activity and can be sexually transmitted. It can be treated with antibiotics such as metronidazole or clindamycin.

Vaginal Yeast Infection or valvovaginal candidiasis is a common cause of vaginal irritation. Several factors are associated with increased symptomatic yeast infection in women, including pregnancy, uncontrolled diabetes mellitus, and use of oral contraceptives or antibiotics. Other factors that may increase the incidence of yeast infection include using douches, perfumed feminine hygiene sprays, and topical antimicrobial agents, and wearing tight, poorly ventilated clothing and underwear. Whether or not yeast can be transmitted sexually is unknown. Various antifungal vaginal medications are available. These include antifungal creams, tablets, or suppositories (butoconazole, miconazole, clotrimazole and tioconazole), over-the-counter for use in the vagina.

Trichomaniasis is commonly referred to as "trich" and is a common STD. It is caused by a single-celled protozoan parasite, *Trichomonas Vaginalis*. Metronidazole is the drug used for treatment.

Gynecologic Oncology:

Intravaginal administration of chemotherapy has been evaluated for the treatment of vaginal and cervical dysplasias. The rational is based on the assumption that higher localized levels can be achieved at a fraction of the intravenous dose with minimal systemic side effects. A case report in 1975 was the first to describe the topical administration of 5-flurouracil (5-FU) for treatment of multifocal vaginal intraepithelial neoplasia. Twice daily administration of 5% 5-FU cream for two weeks resulted in benign cytological findings for up to a 15-month follow-up period. However, evidence of excoriation and thinning of the vaginal wall was noted one month after treatment. This resulted in some dyspareunia for up to 7 months. Similar efficacy and side effects were later noted using different 5-FU concentrations and dosing regimens. In another study, the administration of 20% 5-FU over monthly. 5-day courses in patients with post-irradiation vaginal carcinoma in-situ indicated that seven of the eight women studied had an initial complete response with three of the patients developing a recurrence after treatment was stopped. Re-treatment, however, resulted in a complete response in two of the three recurrences. Meanwhile, it was noted that most of the patients developed vulvovaginitis that was controlled by sitz baths and analgesics. Human Papillomavirus (HPV)-associated lesions of the vulva and vagina have been treated with topical 5-FU as well. Prophylactic topical 5-FU following ablative treatment was studied using biweekly doses of 5% 5-FU creams for six months. Recurrences developed in 13% of the cases as compared to 35% in the control group. It was also noted that maintenance therapy was most effective in women with multiple lesions, multiple organ involvement (vulva, vagina, cervix, anus, distal urethra), or a depressed immune system. Similar findings were noted using a once-a-week dosing regimen. In terms of side-effects, however, long-term topical administration of 5-FU can lead to chronic ulcerative changes in the vagina, particularly after 10 weeks of therapy. Associated symptoms also included sero-sanguinous or watery discharge, post-coital spotting or bleeding, irregular bleeding, and pain. Conservative treatment with estrogens and/or cauterizing agents did not facilitate healing. However, excision of the ulcer with primary closure was found to be curative.

The treatment of cervical intraepithelial neoplasia (CIN) and its effect on the regression CIN II with topically administered all-trans-retinoic acid (RA) has been studied. The device used to deliver RA was a collagen sponge inserted into a cervical cap comprised of a bioadhesive hydrogel. Patients returned at 3 and 6 months for follow-up as well as maintenance treatment consisting of daily RA for 2 days. The results showed that locally applied RA (daily for 4 days) led to complete histologic regression of CIN II in 43% of the patients. No treatment effect was observed in cases of severe dysplasia (CIN III). Side effects included cervical inflammation by colposcopic evaluation, mild vaginal inflammation, and vulva burning/irritation during initial treatment. Intravaginal administration of interferon gamma has also been studied for the treatment of CIN. In terms of cervical cancer, some investigators have proposed intravaginal administration of cisplatin. However, very few case reports exist. Thus, any perceived benefit is purely speculative at this time. The preceding discussion illustrates the possible benefit of intravaginal chemotherapy in the treatment of vaginal and even cervical dysplasias. Again, the choice of the chemotherapeutic agent, mode of delivery, and type of delivery system will be equally as important if efficacy is to be optimized.

It is well acknowledged that intravaginal drug delivery is largely in its infancy compared to other routes of drug administration. It is also well recognized that successful development of novel intravaginal drug delivery systems is intimately related to the successful development of novel polymeric carrier systems for optimized drug efficacy, patient compliance, and safety. And this invention deals with novel polymeric systems for intravaginal drug delivery with attributes that exceed those disclosed in the prior art. Examples of intravaginal delivery systems of the prior art which are most relevant to the present invention are summarized below:

(1) U.S. Pat. No. 6,416,780 describes an intravaginal shell or core drug delivery device suitable for administration of female humans or animals comprises testosterone or a testosterone precursor in a polymer matrix, surrounded by a sheath, and is capable of releasing the testosterone or testosterone precursor in a substantially zero-order pattern on a daily basis for at least three weeks. The device is intended to restore circulating testosterone levels to the normal physiological range or to induce supra-therapeutic testosterone levels.

(2) U.S. Pat. Nos. 6,127,327 and 6,086,909 deals with the transvaginal delivery into the uterus and refers to a special circulation which exists between the vagina and the uterus, which permits preferential uptake of the drug into the uterus when the drug is administered intravaginally or transvaginally using an appropriate device. Such device is, preferably, a medicated tampon, vaginal ring, medicated pessary, medicated cervical cup, medicated tablet, medicated suppository or any other device which is suitable for intravaginal insertion.

(3) U.S. Pat. No. 6,416,779 discloses a medicated intravaginal device for delivery of an antifungal, antiviral, antibacterial, trichomonicidal or parasiticidal pharmaceutical agent intravaginally to a female vagina or transvaginally to uterus or general circulation through a vaginal mucosa, said device comprising a vaginal tampon, vaginal ring, vaginal cup, vaginal tablet, vaginal sponge, or vaginal bioadhesive tablet incorporated with a composition comprising from about 0.1 to about 10%, by weight, of an active agent. The antifungal agent is selected from the group consisting of miconazole, terconazole, isoconazole, fenticonazole, fluconazole, nystatin, ketoconazole, clotrimazole, butoconazole, econazole, tioconazole, itraconazole, 5-fluoracil and metronidazole; the antiviral agent selected from the group consisting of acyclovir, femciclovir, valacyclovir and AZT; the antibacterial agent selected from the group consisting of clindamycin, tetracycline, amoxicillin, ampicillin, erythromycin, doxycycline, lumefloxacin, norfloxacin, afloxam, ciproflaxin, azitromycin and cefltoxine; the antichlamydial agent selected from the group consisting of tetracycline, doxycycline and erythromycin; the trichomonicidal or parasiticidal agent selected from the group consisting of metronidazole and clotrimazol.

(4) U.S. Pat. No. 6,299,894 describes a delivery device for the controlled release of the therapeutically active agent gestodene, over a prolonged period of time, at a release rate of 0.1-300 .mu.g/day, said device comprising a core comprising at least said therapeutically active agent, and a membrane encasing said core wherein said membrane is made of an elastomer. According to the invention, the elastomer is a siloxane-based elastomer comprising 3,3,3-trifluoropropyl groups attached to the Si-atoms of the siloxane units, and the release rate of said therapeutically active agent of said delivery device is regulated by the amount of said 3,3,3-trifluoropropyl groups.

The device can be made according to well-known technology, which can be a T-shaped insert made of plastic materials such as polyethylene. The body consists of an elongate member (stem) having at one end a transverse member comprising two wings. The elongate member and the transverse member form a substantially T-shaped piece when the device is positioned in the uterus. The device has an attached thread long enough to protrude out of the cervical canal when the device is in position in the uterus. Intrauterine systems (IUSs) releasing drugs have a drug reservoir adjusted around the elongate member. This drug reservoir is preferably a matrix which consists of the elastomer matrix with the active agent(s) dispersed therein. Preferably, the matrix is encased in a membrane. The membrane is usually made of an elastomer.

(5) U.S. Pat. No. 6,103,256 deals with an intravaginal drug delivery device comprising at least one active agent dispersed in a polymer matrix, wherein the concentration of active agent at the outer surface of the device at the time of use is not substantially higher than the concentration of the active agent in the remainder of the device, a method of treatment therewith and a process for its preparation. According to this invention, a drug such as estrogen may be administered intravaginally using creams, solutions or tablets. However, as with oral administration, a bolus rather than sustained delivery of estrogen is produced which requires multiple doses. In order to achieve controlled, sustained release of estrogen over a period of months, an intravaginal device, conveniently in the shape of a ring, has proved to be most effective. A particular advantage associated with the use of vaginal rings is that these can be self-inserted and removed from the vagina.

(6) U.S. Pat. No. 4,795,761 describes a contraceptive sponge that may be prepared by absorbing the active constituents into a biocompatible, bioinsoluble, non-toxic sponge-like soft polymer. Suitable polymers for this use are well known in the art, for example 2-hydroxyethyl methacrylate. In another aspect of this invention, a controlled delivery device consists of the active constituents absorbed in a biocompatible, bioinsoluble, flexible, silicone rubber matrix, especially a dimethylpolysiloxane.

(7) U.S. Pat. No. 6,572,874 deals with devices, methods, and compositions for vaginal delivery of bisphosphonates. Intravaginal delivery of bisphosphonates is an alternative route for systemic treatment of osteoporosis and other related bone and skeleton diseases. The composition can be formulated as a suppository, cream, gel, foam, ointment, capsule, capsule containing microparticles, free-microparticles, or microcapsules.

(8) U.S. Pat. No. 5,069,906 describes numerous contraceptive devices that have been developed to eliminate the disadvantages of current, reusable diaphragms. Prior art annular devices provide controlled release of surfactant-type spermicides in the vagina, but that does not act as a barrier to sperm deposition on or in the area of the cervix. Devices with compartments that substantially cap or block the cervix and provide controlled release of spermicidal surfactants have been disclosed; however, these devices are not disposable, and they are designed to remain in the vagina and release spermicide during the time between menstrual periods. Because of this length of use, they may develop problems with infection, odor, or discomfort, and they are less suited for women who engage in sexual intercourse infrequently.

(9) U.S. Pat. No. 4,983,393 describes a solid, shaped, integral, solidified composition suitable for use as an intravaginal insert, capable of dissolution or disintegration in the presence of vaginal fluids, and comprising agarose in an amount from about 0.1 percent to about 4 percent by weight, agar in the amount of about 0.1 percent to about 4 percent by weight, saline solution, high molecular weight glycosaminoglycans of about 100,000 Daltons to about 1,000,000 Daltons in an amount from about 0.1 percent to about 20 percent by weight, collagen in an amount from abut 0.1 percent to about 20 percent by weight, fibrin in an amount from about 0.1 percent to about 20 percent by weight and an enzyme selected from the group consisting of agarase, protease, collagenase and saccharidase, said enzyme being present in said composition in an amount from about 0 percent to about 10 percent by weight.

Unfortunately, most of the polymeric carriers used in the prior art and all the ones described above for the production of intravaginal drug delivery systems were non-absorbable/non-biodegradable. This was pointed out in U.S. Pat. Nos. 5,176,907 and 6,503,528 as major drawbacks and attributes of systems based on absorbable/biodegradable polymers were emphasized as discussed below.

For a non-biodegradable matrix, the steps leading to release of the therapeutic agent are water diffusion into the matrix, dissolution of the therapeutic agent, and diffusion-controlled release of agent through polymer matrix. As a consequence, the mean residence time of the therapeutic agent existing in the soluble state is longer for a non-biodegradable matrix than for a biodegradable matrix where extended diffusion times through tortuous channels is not required. Since many pharmaceuticals may have brief activity after solubilization under physiologic conditions in the vagina, it is likely that the therapeutic agent is decomposed or inactivated inside the non-biodegradable matrix before it can be released. This issue is particularly significant for many bio-macromolecules and smaller polypeptides, since these molecules are generally unstable in buffer and have low permeability through polymers. In fact, in a non-biodegradable matrix, many bio-macromolecules will aggregate and precipitate, clogging the channels necessary for diffusion out of the carrier matrix. This problem is largely alleviated by using an absorbable/biodegradable matrix that allows for degradation-controlled release of the therapeutic agent. Absorbable/biodegradable polymers differ from non-absorbable/non-biodegra-dable polymers in that they are absorbed, biodegraded, or simply consumed during therapy. This usually involves breakdown of the polymer to its monomeric subunits, which should be biocompatible with the surrounding tissue. The life of an absorbable/biodegradable polymer in vivo depends on its chemical structure, molecular weight, and degree of crosslinking; the greater the molecular weight and degree of crosslinking, the longer the life. The most highly investigated absorbable/biodegradable polymers are polylactic acid (PLA), polyglycolic acid (PGA), copolymers of PLA and PGA, polyamides, and copolymers of polyamides and polyesters. PLA, sometimes referred to as polylactide, undergoes hydrolytic de-esterification to lactic acid, a normal product of muscle metabolism. PGA, or polyglycolide, is chemically related to PLA and is commonly used for absorbable surgical sutures. However, the use of PGA in controlled-release implants has been limited due to its low solubility in common solvents and subsequent difficulty in fabrication of devices. The copolymers of lactide and glycolide, commonly known as PLGs, are widely used in drug delivery systems for their solubility in common solvents and ease of processing into different forms of devices. An advantage of an absorbable/biodegradable material is the elimination of the need for surgical removal after it has fulfilled its mission. The appeal of such a material is more than simply for convenience. From a technical standpoint, a material that absorbs or biodegrades gradually and is excreted over time can offer many unique advantages.

An absorbable/biodegradable therapeutic agent delivery system has several additional advantages: (1) the therapeutic agent release rate is amenable to control through variation of the matrix composition; (2) implantation can be done at sites difficult or impossible for retrieval; and (3) delivery of unstable therapeutic agents is more practical. This last point is of particular importance in light of the advances in molecular biology and genetic engineering which have led to the commercial availability of many potent bio-macromolecules. The short in vivo half-lives and low gastrointestinal (GI) tract absorption of these polypeptides render them totally unsuitable for conventional oral or intravenous administration. Also, because these substances are often unstable in buffer, such polypeptides cannot be effectively delivered by pumping devices.

In its simplest form, an absorbable/biodegradable therapeutic agent delivery system consists of a dispersion of the drug solutes in a polymer matrix. The therapeutic agent is released as the polymeric matrix decomposes, or biodegrades into soluble products that are excreted from the body. Several classes of synthetic polymers, including polyesters, polyamides, polyurethanes, polyorthoesters, and polyanhydrides have been studied for this purpose.

Canadian Patent No. 2,420,348 is directed to a non-hormonal, biodegradable intravaginal device for the delivery of spermiostatic, spermicidal and anti-infectious agents. The device, subject of that patent, was described as a flexible structure, impregnated with an effective concentration of biocompatible spermiostatic agents and/or spermicidal agents and/or anti-infective agents. The basic design of the delivery vehicle was described as a hydrogel core-sheath configuration made of biocompatible and biodegradable polymers, which may be either natural and/or synthetic. The biodegradable hydrogel core or matrix component of the device comprises a polysaccharide selected from the group consisting of dextran-maleic acid, dextran-acrylate and dextran-allyl isocyanate, wherein said hydrogel matrix is coated with one or more biodegradable polyglycolide(s), polylactide(s), copolymers of polyglycolide and polylactide and mixture thereof. The spermiostatic, agent subject of CA 2,420,348, is selected from the group consisting of calcium chloride, ferrous sulfate, copper sulfate, ferrous gluconate and mixtures thereof. The patent also disclosed a method for maintaining the vaginal pH at about 5.6 using L-ascorbic acid as part of the matrix composition. In addition to its use as a pH controlling agent, L-ascorbic acid established property as a reducing agent was associated with its effect on increasing the viscosity of the cervical mucus, through conformational changes, and hence interfere with sperm mobility.

Meanwhile, it was noted in U.S. Pat. No. 5,176,907 that all prior art pertaining to absorbable/biodegradable polymers possess some degree of imperfection, such as weak mechanical strength, unfavorable degradation characteristics, toxicity, inflexibility, or fabrication difficulty. Interestingly, a number of similar design defects are implicit in the teaching of CA 2,420,348 where (1) an aqueous hydrogel matrix is coated with a hydrolyzable polyester coating, which represents a chemical incompatibility that cannot be tolerated in any product with an acceptable shelf-life; (2) a hydrophobic coating is applied onto an aqueous matrix, and hence creates an opportunity for cracking and peeling of said coating; and (3) a hydrogel matrix having no mechanical strength is not expected to provide the required resistance to dislocation and subsequent outward migration from the vagina. Although these absorbable/biodegradable polymers have a broad range of potential utility, there is no one single material available that could satisfy all requirements imposed by different applications. Accordingly, there is a definite need to develop new absorbable/biodegradable polymers in traditional or novel forms of drug delivery systems. This provided an incentive to pursue the novel delivery systems subject of this invention. And contrary to all the bioabsorbable/biodegradable polymers of the prior art, the present invention deals with a novel fiber-reinforced device for the intravaginal release of bioactive agents that is controlled not only by the drug/matrix interaction, but also by the properties of the reinforcing fiber component of the device. Such a novel device allows its applicability to a broad range of bioactive agents at a wide range of therapeutically effective dose.

SUMMARY OF THE INVENTION

This invention deals with a controlled drug release device comprising a partially or fully absorbable, fiber-reinforced composite ring system comprising an absorbable or non-absorbable matrix, an absorbable, reinforcing fibrous construct and an absorbable coating to provide three modes of controlling the release of bioactive agents and one mode for modulating the mechanical property of the ring in a body cavity during device functional use. For partially absorbable ring systems, the drug release is dependent initially on the diffusion rate of the drug through the matrix and the absorbable coating. As the latter degrades with time, the diffusion through the matrix prevails. Meanwhile, as the absorbable fibrous reinforcing construct undergoes degradation with time, the mechanical strength of the composite ring decreases to provide the desired mechanical strength retention profile. For a fully absorbable composite ring system, the degradation of the matrix offers an additional mode of controlling the release profile as compared with the partially absorbable counterpart. In effect, the present invention deals with a fiber-reinforced composite ring system for the controlled release of at least one bioactive agent comprising a biocompatible matrix reinforced with an absorbable/biodegradable fibrous construct capable of providing the mechanical properties needed for inserting and maintaining said ring in a body cavity for the desired period of time, and wherein the absorbable/biodegradable reinforcing fibers are made primarily of one or more cyclic monomer(s) including glycolide, l-lactide, .epsilon.-caprolactone, p-dioxanone, and trimethylene carbonate.

One aspect of this invention deals specifically with a fiber-reinforced composite ring for the controlled release of at least one bioactive agent comprising a biocompatible matrix reinforced with absorbable/biodegradable fibers capable of providing the mechanical properties needed for inserting and maintaining said ring in a body cavity for the desired period of time, wherein the absorbable/biodegradable reinforcing fibers are made primarily of one or more cyclic monomer(s) including glycolide, l-lactide, .epsilon.-caprolactone, p-dioxanone, and trimethylene carbonate, wherein both the reinforcing fibers and matrix are absorbable/biodegradable.

Another aspect of this invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time, wherein the absorbable/biodegradable reinforcing fibers are made primarily of one or more cyclic monomer(s) including glycolide, l-lactide, .epsilon.-caprolactone, p-dioxanone, and trimethylene carbonate, wherein the reinforcing fibers are absorbable/biodegradable and the matrix is non-absorbable/non-biodegradable.

Another aspect of this invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time, and wherein the absorbable/biodegradable reinforcing fibers are made primarily of one or more cyclic monomer(s) including glycolide, l-lactide, .epsilon.-caprolactone, p-dioxanone, and trimethylene carbonate, wherein the fibers are in the form of a circularly configured construct, with protruding side loops made of monofilament yarn or twisted and braided multifilament yarn based on one or more type(s) of absorbable polymers and the matrix comprising an absorbable/biodegradable polymer comprising ester and urethane linkages.

Another aspect of this invention pertains to a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time, wherein the reinforcing fibers are absorbable/biodegradable and the matrix is non-absorbable/non-biodegradable, wherein the fibers are in the form of circularly configured construct, with protruding side loops, made of monofilament yarn or twisted and/or braided multifilament based on one or more type(s) of absorbable polymer and the matrix comprising an absorbable/biodegradable polymer comprising ester and urethane linkages.

Another aspect of the invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time, wherein the reinforcing fibers are absorbable/biodegradable and the matrix is non-absorbable/non-biodegradable, wherein the non-absorbable matrix comprising a methacrylate polymer derived from at least one alkyl methacrylate monomer, and wherein the methacrylate polymer is derived from one or more alkyl methacrylate monomer(s) and N-vinyl pyrrolidone.

Another aspect of this invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time, wherein the reinforcing fibers are absorbable/biodegradable and the matrix comprising absorbable and non-absorbable components, wherein the non-absorbable component of the matrix comprising poly dimethylsiloxane and the absorbable/biodegradable component comprising polymer chains with ester or ester-urethane linkages and wherein the non-absorbable component of the matrix comprising methacrylate-derived chains.

Another aspect of the invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time wherein the composite comprises a water-soluble excipient to aid the release of the drug or a retardant additive to slow down such release.

Another aspect of the invention pertains to a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time wherein the composite comprises a polymeric outer coating to modulate the early release of the bioactive agent(s) and the coating is preferably a bioadhesive.

A specific aspect of this invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time wherein the matrix is microporous.

Another specific aspect of the invention deals with a fiber-reinforced composite ring for the controlled release of at least one bioactive agent comprising a biocompatible matrix reinforced with absorbable/biodegradable fibers capable of providing the mechanical properties needed for inserting and maintaining said ring in a body cavity for the desired period of time wherein the matrix comprises a cyclodextrin or cyclodextrin derivatives.

A specific aspect of this invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time, wherein said ring is suited for intravaginal placement for the controlled release of one or more active agent(s) for achieving contraception, selected from the group represented by spermiostatic, spermicidal and hormonal agents and a viscosity modifier of the vaginal mucus. Such an intravaginal ring can be used for the controlled release of one or more bioactive agent(s) selected from the group used for contraception, labor induction, intravaginal and transvaginal prevention or treatment of bacterial, fungal, viral or parasitic infection, cervical cancer, and ovarian cancer, wherein the composition is designed for the release of at least one bioactive agent for providing hormone replacement therapy, achieving contraception, treating infertility, managing infectious diseases, and use in gynecological cancer. The intravaginal ring may also comprise an antifertility drug, such as testosterone and testosterone precursor, a spermicidal agent, or sperm immobilizer, and bisphosphonate. Additionally, the intravaginal ring can be used for the controlled release of drugs having antiprogestinic anesthetic, analgesic, anti-inflammatory, antimicrobial, antiviral, or antipsychotic properties. The intravaginal ring can also be used for the controlled delivery of antibodies especially the monoclonal types, immunomodulator vaccines especially the recombinant types, and hematopoietic growth factors.

A more general aspect of this invention deals with a fiber-reinforced composite ring for the controlled release of at least one bioactive agent comprising a biocompatible matrix reinforced with absorbable/biodegradable fibers capable of providing the mechanical properties needed for inserting and maintaining said ring in a body cavity for the desired period of time wherein the ring is suited for intraperitoneal placement for the controlled release of one or more bioactive agent(s) having anesthetic, analgesic, anti-inflammatory, antimicrobial, antibacterial, antifungal, antiviral, antipsychotic, antiadhesion, and antineoplastic properties.

Another aspect of the invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time wherein the matrix contains one or more bioactive agent(s) with modulated solubility in the polymeric matrix, wherein said bioactive agent is an ionic conjugate of a basic antimicrobial drug having lower solubility in the polymeric matrix than the free-basic drug, and wherein said basic drug is selected from the group represented by metronidazole and miconazole and the acidic component of the conjugate is pamoic acid or its monosodium salt.

Another aspect of this invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time wherein such ring is used as a component of an orthopedic prosthesis and a subcutaneous device.

DETAILED DESCRIPTION OF PREFERRED EMBODIMENTS

This invention deals with a fiber-reinforced composite ring system for the controlled release of one or more bioactive agent(s) at the desired biological sites, which may entail intravaginal, intraperitoneal, and subcutaneous administration of such agent(s). The composite ring system is designed to modulate the bioactive agent(s) release profile as well as the mechanical property of the ring, in part or totally through the controlled degradation of the absorbable components of the composite system.

The composite ring can be fully or partially absorbable/biodegradable and consist of a flexible matrix, which may or may not be microporous and is reinforced with multifilament or monofilament yarn made of a high modulus polymer. The yarn is configured in the form of a circular or mostly circular structure. While being absorbable/biodegradable or non-absorbable/non-biodegradable, the matrix is designed to be the primary carrier of the bioactive agents, and its physicochemical interaction with the bioactive agent(s) is designed to modulate the diffusion and release of said bioactive agent(s). The reinforcing fiber is made of an absorbable/biodegradable polymer and is designed to (1) provide sufficient mechanical strength and resilience to allow facile insertion of the ring and its maintenance for the desired period of time at the vaginal site; and (2) exhibit a certain strength retention profile so as to be used in controlling the decrease in the mechanical properties and resilience of the vaginal ring with time. In a typical scenario, the reinforcing fibers lose, gradually, their mechanical strength over three to four weeks leading to collapse of the ring and its extrusion from the vaginal canal aided by exiting vaginal fluids. If the matrix is absorbable, its absorption profile can be modulated to synchronize with the gradual mechanical failure of the reinforcing fibers leading to extrusion of flexible components of the ring. On the other hand, if the matrix is non-absorbable, the collapsed ring will extrude as one unit or can be easily removed manually by the patient or physician. To modulate the release profile of the bioactive agent(s) (1) the ring may be coated with a polymeric barrier to control early burst; (2) a water-soluble excipient may be incorporated in the matrix to facilitate the agent(s) release; and (3) the matrix may be designed to be microporous to increase the drug diffusion.

This invention deals with a controlled drug release device comprising a partially or fully absorbable, fiber-reinforced composite ring system comprising an absorbable or non-absorbable matrix, an absorbable, reinforcing fibrous construct and an absorbable coating to provide three modes of controlling the release of bioactive agents and one mode for modulating the mechanical property of the ring in a body cavity during device functional use. For partially absorbable ring systems, the drug release is dependent initially on the diffusion rate of the drug through the matrix and the absorbable coating. As the latter degrades with time, the diffusion through the matrix prevails. Meanwhile, as the absorbable fibrous reinforcing construct undergoes degradation with time, the mechanical strength of the composite ring decreases to provide the desired mechanical strength retention profile. For a fully absorbable composite ring system, the degradation of the matrix offers an additional mode of controlling the release profile as compared with the partially absorbable counterpart. In effect, the present invention deals with a fiber-reinforced composite ring system for the controlled release of at least one bioactive agent comprising a biocompatible matrix reinforced with an absorbable/biodegradable fibrous construct capable of providing the mechanical properties needed for inserting and maintaining said ring in a body cavity for the desired period of time, and wherein the absorbable/biodegradable reinforcing fibers are made primarily of one or more cyclic monomer(s) including glycolide, l-lactide, .epsilon.-caprolactone, p-dioxanone, and trimethylene carbonate.

One aspect of this invention deals specifically with a fiber-reinforced composite ring for the controlled release of at least one bioactive agent comprising a biocompatible matrix reinforced with absorbable/biodegradable fibers capable of providing the mechanical properties needed for inserting and maintaining said ring in a body cavity for the desired period of time, wherein the absorbable/biodegradable reinforcing fibers are made primarily of one or more cyclic monomer(s) including glycolide, l-lactide, .epsilon.-caprolactone, p-dioxanone, and trimethylene carbonate, wherein both the reinforcing fibers and matrix are absorbable/biodegradable.

Another aspect of this invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time, wherein the absorbable/biodegradable reinforcing fibers are made primarily of one or more cyclic monomer(s) including glycolide, l-lactide, .epsilon.-caprolactone, p-dioxanone, and trimethylene carbonate, wherein the reinforcing fibers are absorbable/biodegradable and the matrix is non-absorbable/non-biodegradable.

Another aspect of this invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time, and wherein the absorbable/biodegradable reinforcing fibers are made primarily of one or more cyclic monomer(s) including glycolide, l-lactide, .epsilon.-caprolactone, p-dioxanone, and trimethylene carbonate, wherein the fibers are in the form of a circularly configured construct, with protruding side loops made of monofilament yarn or twisted and/or braided multifilament yarn based on one or more type(s) of absorbable polymers and the matrix comprising an absorbable/biodegradable polymer comprising ester and urethane linkages.

Another aspect of this invention pertains to a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time, wherein the reinforcing fibers are absorbable/biodegradable and the matrix is non-absorbable/non-biodegradable, wherein the fibers are in the form of circularly configured construct, with protruding side loops, made of monofilament yarn or twisted and/or braided multifilament based on one or more type(s) of absorbable polymer and the matrix comprising an absorbable/biodegradable polymer comprising ester and urethane linkages.

Another aspect of the invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time, wherein the reinforcing fibers are absorbable/biodegradable and the matrix is non-absorbable/non-biodegradable, wherein the non-absorbable matrix comprising a methacrylate polymer derived from at least one alkyl methacrylate monomer, and wherein the methacrylate polymer is derived from one or more alkyl methacrylate monomer(s) and N-vinyl pyrrolidone.

Another aspect of this invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time, wherein the reinforcing fibers are absorbable/biodegradable and the matrix comprising absorbable and non-absorbable components, wherein the non-absorbable component of the matrix comprising poly dimethylsiloxane and the absorbable/biodegradable component comprising polymer chains with ester or ester-urethane linkages and wherein the non-absorbable component of the matrix comprising methacrylate-derived chains.

Another aspect of the invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time wherein the composite comprises a water-soluble excipient to aid the release of the drug or a retardant additive to slow down such release.

Another aspect of the invention pertains to a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time wherein the composite comprises a polymeric outer coating to modulate the early release of the bioactive agent(s) and the coating is preferably a bioadhesive.

A specific aspect of this invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time wherein the matrix is microporous.

Another specific aspect of the invention deals with a fiber-reinforced composite ring for the controlled release of at least one bioactive agent comprising a biocompatible matrix reinforced with absorbable/biodegradable fibers capable of providing the mechanical properties needed for inserting and maintaining said ring in a body cavity for the desired period of time wherein the matrix comprises a cyclodextrin or cyclodextrin derivatives.

A specific aspect of this invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time, wherein said ring is suited for intravaginal placement for the controlled release of one or more active agent(s) for achieving contraception, selected from the group represented by spermiostatic, spermicidal and hormonal agents and a viscosity modifier of the vaginal mucus. Such an intravaginal ring can be used for the controlled release of one or more bioactive agent(s) selected from the group used for contraception, labor induction, intravaginal and transvaginal prevention or treatment of bacterial, fungal, viral or parasitic infection, cervical cancer, and ovarian cancer, wherein the composition is designed for the release of at least one bioactive agent for providing hormone replacement therapy, achieving contraception, treating infertility, managing infectious diseases, and use in gynecological cancer. The intravaginal ring may also comprise an antifertility drug, such as testosterone and testosterone precursor, a spermicidal agent, or sperm immobilizer, and bisphosphonate. Additionally, the intravaginal ring can be used for the controlled release of drugs having antiprogestinic anesthetic, analgesic, anti-inflammatory, antimicrobial, antiviral, or antipsychotic properties. The intravaginal ring can also be used for the controlled delivery of antibodies especially the monoclonal types, immunomodulator vaccines especially the recombinant types, and hematopoietic growth factors.

A more general aspect of this invention deals with a fiber-reinforced composite ring for the controlled release of at least one bioactive agent comprising a biocompatible matrix reinforced with absorbable/biodegradable fibers capable of providing the mechanical properties needed for inserting and maintaining said ring in a body cavity for the desired period of time wherein the ring is suited for intraperitoneal placement for the controlled release of one or more bioactive agent(s) having anesthetic, analgesic, anti-inflammatory, antimicrobial, antibacterial, antifungal, antiviral, antipsychotic, antiadhesion, and antineoplastic properties.

Another aspect of the invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time wherein the matrix contains one or more bioactive agent(s) with modulated solubility in the polymeric matrix, wherein said bioactive agent is an ionic conjugate of a basic antimicrobial drug having lower solubility in the polymeric matrix than the free-basic drug, and wherein said basic drug is selected from the group represented by metronidazole and miconazole and the acidic component of the conjugate is pamoic acid or its monosodium salt.

Another aspect of this invention deals with a fiber-reinforced composite ring for the controlled release of at least one bioactive agent comprising a biocompatible matrix reinforced with absorbable/biodegradabl-e fibers capable of providing the mechanical properties needed for inserting and maintaining said ring in a body cavity for the desired period of time wherein such ring is used as a component of an orthopedic prosthesis and a subcutaneous device.

Another aspect of the invention deals with a matrix comprising absorbable and non-absorbable components. The former can represent a minor physical segment of the ring that degrades along with the reinforcing fibers and allow the major non-absorbable components of the ring to acquire a practically linear form, which will extrude easily from the vagina.

One specific aspect of this invention deals with a partially or fully absorbable intravaginal device for the controlled release of bioactive agents including infertility, antimicrobial, antiviral, and oncologic agents. Another specific aspect of this invention deals with a ring-type, flexible, bioactive device comprising absorbable/biodegradable components capable of modulating the shape of the device for ease of removal or extrusion from the vaginal cavity at the conclusion of the functional period of said bioactive device. Yet another aspect of this invention deals with a fully absorbable ring comprising an absorbable flexible matrix reinforced with a high-strength, rigid fibrous construct. A more specific aspect of this invention deals with a composite ring comprising an absorbable matrix consisting of one or more of the following sequence(s) which are disposed randomly as short segments or blocks along the polymer chain: ester, ether, urethane, and peptide, wherein said matrix is reinforced with a fiber made of polymers which comprise ester sequences derived from one or more of the following monomer(s): glycolide, lactide, trimethylene carbonate, p-dioxanone, and .epsilon.-caprolactone. The reinforcing component of the composite is based on a high strength, high modulus, fibrous construct made of a polymer derived from one or more of the following cyclic monomer(s): glycolide, lactide, .epsilon.-caprolactone, trimethylene carbonate, and p-dioxanone.

Another feature of this invention is that the composite vaginal ring is designed to release the bioactive agent over a period of one day to six months. Other aspects of this invention relate to the chemical and physical properties of the matrix material, which can (1) be absorbable/biodegradable or non-absorbable/non-biodegradable (or biostable); (2) be based primarily on one or more synthetic polymer(s) such as polyesters, polyether-esters, polyether-ester-urethanes, or naturally derived polymers such as chitosan, alginate, casein, and collagen; (3) be based on a combination of a synthetic and a naturally derived polymer, such as cyclodextrin or cyclodextrin derivatives; and/or (4) comprise linear and/or crosslinked chain molecules. Another aspect of this invention relates to the chemical and physical properties of the reinforcing fiber which can be (1) made of a continuous multifilament or monofilament yarn of an absorbable, biodegradable polymer with intrinsic or engineering modulus in the moderate or high range; (2) twisted chitosan staples which may be treated with an absorbable synthetic coating to increase its engineering modulus; (3) based on a polyester or copolyester derived from one or more of the following monomer(s): glycolide, l-lactide, dl-lactide, trimethylene carbonate, p-dioxanone, .epsilon.-caprolactone, morpholinedione; (4) based on a segmented or block copolymer made by end-grafting polyalkylene dicarboxylate, such as polyethylene succinate, with one or more of the cyclic monomer(s) of item 3; and (5) made of twisted yarn, braid, twisted/coated staples, or non-woven fabric in the form of a ring structure. For a non-absorbable matrix, a useful polymeric material can be based on (1) poly dimethyl siloxane with and without aromatic sequences serving as a modifier and crosslinked siloxane-based system; and (2) a methacrylate polymer derived from one or more alkyl methacrylate(s) such as n-hexyl methacrylate, n-butyl methacrylate, with our without a more hydrophilic monomer such as vinyl acetate and or N-vinyl pyrrolidone. In another aspect of this invention, the reinforcing yarn may be chemically treated primarily at its surface to create basic or acidic groups for binding, ionically, acidic or basic drugs for providing an additional mode for controlling the release of potent drug other than simple diffusion through the matrix or through physical liberation as the matrix degrades, as in the case of absorbable/biodegradable matrices. One additional aspect is the cross-section form and dimension of the composite vaginal ring wherein (1) the average diameter may vary from 1 to less than 25 mm; and (2) shape can vary from a perfect circle to an ellipse to practically a ribbon, depending on the composition and physical properties of the matrix and reinforcing fibers.

From a functional and fiber-loading perspective, the fiber-reinforced vaginal ring subject of this invention can (1) contain between 0.0001% to 40% of its weight of active bioactive agent(s); and (2) designed to release at least one bioactive agent for providing hormone replacement therapy, achieving contraception, treating infertility, managing infectious diseases, and use in gynecologic oncology. Thus the bioactive, fiber-reinforced vaginal ring may contain natural or synthetic estrogens and progestational agents for contraception, micronized progesterone or LH-releasing hormone and its synthetic analogs for infertility, prostaglandin analogs for labor induction/augmentation, somatostatin or its synthetic analogs, anti-neoplastic/angiogenic drugs such as paclitaxel, cisplatin, 5-FU, and curcumin, non-steroidal anti-inflammatory drugs such as naproxen, immunomodulating agents, antibiotic and anti-mycotic agents, spermicidal agents, and virucidal agents. The bioactive, fiber-reinforced vaginal ring may be designed to be a more effective controlled release system than most orally, transdermally, inhalable, injectable drugs that are commonly are used for (1) relieving headache; (2) treating allergy; (3) treating the common cold; (4) treating cervical or uterine cancer; (5) treating flue infection; (6) treating human immunodeficiency virus (HIV); (7) treating different forms of bacterial, fungal, and viral infections, particularly those pertaining to the female genital system; (8) administering spermicidal agents or sperm immobilizer drugs having anesthetic, analgesic, antipyretic, antiprogestinic, and antipsychotic properties. The fiber-reinforced vaginal ring can also be used for the delivery of antibodies, especially the monoclonal types of immunomodulators, vaccines especially the recombinant types, insulin, and hematopoietic growth factor. The fiber-reinforced vaginal ring may be used to deliver potent agents for (1) facilitating labor induction or controlled abortion; (2) treatment of intravaginal or transvaginal bacterial, fungal, viral, or parasitic infections; and (3) treating osteoporosis and especially those based on bisphosphonates.

Typically, vaginal drugs such as miconazole, acyclovir, clotrimazole, ticonazole, metronidazole, hormones (such as estrogen), sulfas and nystatin may be incorporated within the intravaginal device in suitable amounts for sustained release over a fixed period of time. Specifically suitable drugs which may be used include sulfabenzamide, sulfacetamide, sulfacytine, sylfatriazole and the like. Benzetimine, a non-steroid anti-inflammatory drug, and alpha-lactalbumin, a protein found I milk, may also be included if desired. Monoclonal antibodies such as those useful against cell surface components or against pathogenic organisms such as the human immunodeficiency (HIV) family of viruses, may be incorporated into the device of the present invention for ultimate intravaginal release. Thus, the present device is usefully employed as a drug carrier for spermiostatic agents, spermicides, gemicides, and virucides. Combinations of these materials in safe and effective amounts may be used as desired. Typically, the range of drug additives may be in the amount of about 0.001 percent to about 10.0 percent by weight.

Additional illustrative examples associated with this invention are outlined below.

EXAMPLE 1

Preparation of 25/75 Copolymer (P-VP-BMA) of N-Vinyl Pyrrolidone (VP) and n-Butyl Methacrylate (BMA)

This entailed a two-step synthesis based on two polymerization charges. The first charge was made of N-vinyl pyrrolidone (VP)-rich comonomer mixture. Thus VP (0.163 mole), n-butyl methacrylate (0.0654 mole), dioxane (55 ml), and 2,2'-azo-bis-isobutyronitrile (2.31 mmole) were mixed under nitrogen atmosphere. The mixture was sparged with nitrogen for two minutes, added to a flask equipped for mechanical stirring that was kept under a positive nitrogen pressure, and mechanically stirred at 60 rpm in a 65° C. silicon oil bath for a total of 30 minutes. For the second charge, n-butyl methacrylate (0.422 mole), 1,4-dioxane (55 ml), and 2-2' azo-bis-isobutyronitrile (2.31 mmole) were mixed under dry nitrogen. The mixture was sparged with nitrogen for 2 minutes and added to the product of the first charge over a period of 18 hours. The reaction was then allowed to continue at 65° C. for an additional 30 minutes.

The polymer was precipitated in an excess of ice water contained in a stirring blender, filtered using a fritted funnel. The isolated product was then blended in methanol at −60° C., filtered and dried under reduced pressure at room temperature. The dried polymer was dissolved in chloroform to form a 20 weight percent solution, and then precipitated in −60° C. methanol. The precipitate was isolated by filtration and then dissolved in chloroform, poured onto a Teflon tray, and dried to constant weight under reduced pressure at 45° C.

EXAMPLE 2

Preparation of Polyethylene Glycol 400 (PEG-400) Capped with Itaconic Anhydride to Form PEG-400-IT The PEG-400 was predried at 100° C. under reduced pressure for about 30 minutes. The dried PEG-400 (1 mole) was mixed with itaconic anhydride (2 moles) and heated while stirring mechanically at 110° C. for 80 minutes. The structure of capped product (PEG-400-IT) was verified using IR and NMR, and its molecular weight and purity were determined by GPC (using dichloromethane as a solvent). To stabilize the itaconic anhydride in the initial charge and the resulting PEG-400-IT against premature free-radical polymerization, hydroquinone was initially incorporated into the reaction mixture at a level of 0.01 percent by weight. The capped product was also stored under nitrogen at 4° C.

EXAMPLE 3

Preparation of 95/5 F-Caprolactone/Glycolide Copolymer Coating (CT-1)

The CT-1 copolymer was prepared by the copolymerization of .epsilon.-caprolactone (0.625 mole) with glycolide (32.3 mmole) in the presence of glycolic acid (3.756 mmole) as the initiator and stannous octanoate (0.1247 mmole as 0.2M solution in toluene) as the catalyst. The polymerization was conducted in a mechanically stirred reactor under a dry nitrogen atmosphere at 150° C. for 6.25 hours. At the conclusion of the polymerization, as determined by GPC, traces of unreacted monomer were removed by distillation under reduced pressure. The composition of the purified polymer was verified by IR and NMR. The polymer was shown to melt at 55° C. as determined by DSC.

EXAMPLE 4

Preparation of Partially Absorbable Vaginal Ring Reinforced with 95/5 Glycolide/l-Lactide Copolymeric Monofilament Yarn (IVR-I)

Listed below are the components of an active matrix that are mixed and introduced into a closed, 2-part Teflon mold having a ring-type cavity (ID=4.3 cm, OD=5.5 cm), an inlet for introducing the reactants, and an outlet to exit displaced dry nitrogen used in pre-purging the dry mole. Twisted monofilament yarn (diameter=0.2 mm) of 95/5 glycolide/l-lactide copolymer constructed into a ring configuration having side barbs (weight=0.5 g, outside diameter=4.9 cm) was placed centrally (by virtue of the side barbs) into the cavity of the lower component of the mold to allow for equidistant placement between the OD and ID of the curved ring system. A fraction of the components listed below, which have been mixed under nitrogen, was charged into the lower half of the open mold under a nitrogen atmosphere. The top part was then placed on the lower part, and the mold was closed and mechanically secured. The remaining fraction of the mixed components was then injected into the mold through the feed port.

List of Mixed Matrix Components

| | |
|---|---|
| Lauryl methacrylate | 3.5 g |
| 25/75 copolymer of N-vinyl pyrrolidone and n-butyl methacrylate (from Example 1) | 2.4 g |
| Polyethylene glycol 400 capped with itaconic anhydride (from Example 3) | 0.6 g |
| 2,2'-Azo-bis-isobutyronitrile | 0.2 g |
| Solid spermiostatic drug mixture | 0.6 g |

The charged mold is heated at 65° C. for 16 hours. At the conclusion of the heating cycle, the ring was removed, coated with 95/5 poly(caprolactone-co-glycolide)(from Example 3) by dipping in a 5 percent solution of methylene chloride followed by drying. The dried, coated ring was then used for testing its degradation in a phosphate buffered solution at 37° C. as a function of time for: (1) the drug release profile at pH 4.5; and (2) compressibility retention profile, as measured in terms of the force required to attain a predetermined degree of deflection, using an MTS Universal Tester (858 MiniBionix) in the compression mode, as described in Example 21.

EXAMPLE 5

Preparation of Partially Absorbable Vaginal Ring Reinforced with Segmented 88/12 l-Lactide/Trimethylene Carbonate Braided Multifilament Yarn (IVR-II)

IVR-II was prepared in the same fashion as IVR-I with the exception of using (1) braided multifilament yarn of segmented 88/12 l-lactide/trimethylene carbonate dyed braided multifilament [prepared as described in U.S. Pat. No. 6,342,065 (2002) and containing 0.05 percent D&C Violet #2]; and (2) a solid spermatostatic agent comprising a 50/50 mixture of ferrous gluconate and ascorbic acid.

EXAMPLE 6

Preparation of 30/70 PEG-400/.epsilon.-Caprolactone Block Copolymer (PEG-CL-1)

The PEG-400 was predried as described in Example 2. The copolymerization was carried out in a stirred reactor under dry nitrogen atmosphere using dried PEG-400 (30 g), .epsilon.-caprolactone (70 g), and stannous octanoate as a catalyst (at monomer to catalyst molar ratio of 6000/1). The copolymerization was conducted at 150° C. and completed at 10 hours as determined by GPC (using dichloromethane as a solvent). Traces of unreacted caprolactone were removed by distillation at 100° C. under reduced pressure. The identity of PEG-CL-1 was verified by IR and NMR and its molecular weight was determined by GPC ($M_n$=2.9 kDa; $M_w$=3.2 kDa). The thermal properties were determined by DSC and showed a $T_m$ of 36° C. and $\Delta H_f$ of 23 J/g.

EXAMPLE 7

End-capping PEG-CL-1 with Itaconic Anhydride to Produce PEG-CL-1-IT

The PEG-CL-1-IT was prepared and characterized under conditions similar to those used in Example 2, with the exception of substituting PEG-400 with PEG-CL-1 from Example 6. The product was stabilized with hydroquinone as described in Example 2. The composition of the product was verified by NMR and IR; the thermal properties were determined by DSC indicated by a $T_m$ of 35° and $\Delta H_f$ of 12 J/g.

EXAMPLE 8

Preparation of 25/75 Copolymer (P-VP/HMA) of N-Vinyl Pyrrolidone (VP) and n-Hexyl Methacrylate (HMA)

Copolymer (P-VP/HMA) was made, purified, and characterized following conditions similar to those in Example 1, with the exception of substituting n-butyl methacrylate with n-hexyl methacrylate.

EXAMPLE 9

Preparation of Itaconic Anhydride Capped PEG-CL-1 Copolyester (PEG-CL-1-IT)

Using PEG-CL-1 from Example 6 and itaconic anhydride, the capped product PEG-CL-1-IT was prepared and characterized as described for PEG-400-IT in Example 2. The product was isolated as an off-white solid. The composition of the product was verified by IR and NMR and its thermal properties by DSC. The DSC data indicated a $T_m$ of 35° C. and $\Delta H_f$ of 12 J/g. The molecular weight was determined by GPC ($M_n$=2.8 kDa; $M_w$=3.2 kDa).

EXAMPLE 10

Preparation of Dyed Partially Absorbable Vaginal Ring Reinforced with Segmented 88/12 l-Lactide/Trimethylene Carbonate Braided Multifilament (VR-III)

The IVR-III was prepared, coated, and tested as described in Example 4, with the exception of using the following components per ring:

List of Mixed Components

| | |
|---|---|
| Lauryl methacrylate | 3.5 g |
| 25/75 copolymer of N-vinyl pyrrolidone and n-hexyl methacrylate (from Example 8) | 2.4 g |
| Itaconic anhydride PEG 400/caprolactone block copolymer (from Example 9) | 0.6 g |
| 2,2'-Azo-bis-isobutyronitrile | 0.2 g |
| 0.2 g Ascorbic acid | 0.3 g |
| Ferrous gluconate | 0.3 g |
| D&C Violet #2 | 0.5 mg/g polymer |

EXAMPLE 11

End-grafting a Mixture of PEG-8000 and Trimethylolpropane with Trimethylene Carbonate A mixture of PEG-8000 (40 g), trimethylolpropane (13 g), and trimethylene carbonate (60 g) was charged under a dry nitrogen atmosphere into a dry glass reactor equipped for mechanical stirring. The reactants were heated to 80° C. for 20 minutes to attain a uniform liquid. To this was added stannous octanoate (0.3 mL as a 0.2M solution in toluene) to catalyze the copolymerization of trimethylene carbonate. The copolymerization was conducted practically to completion, as determined by GPC (using methylene chloride as a solvent), by heating while stirring at 150° C. under nitrogen atmosphere for 14 hours. Traces of unreacted monomer were removed by distillation under reduced pressure at 100° C. the purified product was isolated and characterized for identity by IR and NMR and its molecular weight was determined by GPC.

EXAMPLE 12

Preparation of Totally Absorbable Fiber-reinforced Vaginal Ring Using a Polyether-ester Matrix Reinforced with 95/5 Glycolide/l-Lactide Copolymeric Monofilament (IVR-IV)

Using the Teflon mold described in Example 4, precharged with 0.5 g of 95/5 glycolide/l-lactide-based monofilament in a circular (or ring) configuration (with side loops), the matrix components listed below are mixed and introduced into the mold cavity. The ring curing was conducted at 50° C. for 16 hours. At the conclusion of the process, the ring is isolated, processed, coated, and tested as in Example 4.

List of Mixed Matrix Components

| | |
|---|---|
| Hexane diisocyanate | 1.0 g |
| End-grafted mixture of polyethylene glycol 8000 (40 g) and trimethylol propane (13 parts) with trimethylene carbonate (60 parts)(from Example 11) | 5.15 g |
| Solid spermicidal mixed agents (e.g., 50/50 by weight mixture of ascorbic acid and Iron (II) gluconate) | 0.6 g |
| D&C violet #2 | 2.0 mg |

EXAMPLE 13

Preparation of Triaxial 90/10 (molar) .epsilon.-Caprolactone (CL)/Glycolide (G) Copolymer (T-CL/G)

A mixture of CL (449.2 g) and glycolide (50.8 g) was mixed under dry nitrogen atmosphere in a predried reactor equipped for mechanical stirring. The polymerization was conducted under dry nitrogen atmosphere in the presence of trimethylol propane (8.38 g) as the initiator and stannous octanoate (2.73 mL of 0.2M toluene solution) as the catalyst. The polymerization was completed after heating at 150° C. for 11 hours as determined by GPC. Traces of unreacted monomer were removed by distillation at 110° C. under reduced pressure. The molecular weight and thermal properties of the purified polymer were determined by GPC and DSC, respectively. The analytical data are summarized below: $M_n$=17 kDa; $M_w$=25 kDa; $T_m$=44.7.degree. C.; .DELTA.H.sub.f=58.3 J/g

EXAMPLE 14

End-capping T-TMC/G with Itaconic Anhydride to Produce T-TMC/G-IT

The end-capping product (T-TMC/G-IT) was prepared and characterized under conditions similar to those used in Example 2, with the exception of (1) substituting PEG-400 with T-CL/G of Example 13; (2) conducting the reaction at 150° C. for 4 hours; and (3) using a reaction charge consisting of T-TMC/G (220 g) and itaconic anhydride (64.4 g) as well as hydroquinone (111 mg). The capped product was isolated as a viscous liquid. It was characterized for composition by IR and NMR.

EXAMPLE 15

Preparation of Triaxial 95/5 (molar) Trimethylene Carbonate (TMC), Glycolide (G) Copolymer (T-TMC/G)

Using the following reactants and catalysts, the copolymer was prepared, purified, and characterized as described for T-CL/G of Example 13, with the exception of using a polymerization time of 17.5 hours. The reaction product was isolated as a clear liquid having an $M_n$ of 2.4 kDa and $M_w$ of 57 kDa as determined by GPC (using methylene chloride as a solvent).

| | |
|---|---|
| TMC | 456 g |
| Glycolide | 27.3 g |
| Trimethylolpropane | 63.0 g |
| Stannous Octanoate | 1.568 mL (of 0.2M molar solution in toluene) |

The purified polymer was isolated as clear liquid having an $M_n$ of 2.42 kDa and $M_w$ of 5.73 kDa as determined by GPC using dichloromethane as the solvent.

EXAMPLE 16

End-capping T-CL/G with Itaconic Anhydride to Produce T-CL/G-IT

The end-capping product (T-CL/G-IT) of T-CL/G was prepared and characterized under conditions similar to those used in Example 2, with the exception of (1) substituting PEG-400 with T-CL/G of Example 14; (2) conducting the reaction at 150° C. for 4 hours; and (3) using a reaction charge consisting of T-CL/G (100 g), itaconic anhydride (4.083 g), and hydroquinone (50 mg). The capped product was isolated as an off-white solid. It was characterized for composition by IR and NMR and thermal properties by DSC. The DSC data indicated a $T_m$ of 44° C. and .DELTA.H.sub.f of 54 J/g.

EXAMPLE 17

Preparation of Absorbable, Segmented Triaxial Copolyester Coating (CT-2)

The subject copolymer was prepared in two steps following the general procedure described in U.S. Pat. No. 6,462, 169. In this example, the first step entailed the copolymerization of trimethylene carbonate (1.852 mole), .epsilon.-caprolactone (1.852 mole) in the presence of triethanolamine (6.17 mmole) as the initiator and stannous octanoate (0.529 mmole) as the catalyst. The polymerization was conducted in a mechanically stirred reactor under dry nitrogen atmosphere at 180° C. for 1 hour. The product was cooled to 130° C. prior to adding the comonomer charge in the second step. For second step, 1-lactide (2.553 mole) and .epsilon.-caprolactone (0.2837 mole) were added to the product of the first step, and the temperature was raised to 140° C. The reaction was conducted at that temperature for 24 hours, when the conversion was practically complete, as determined by GPC (using methylene chloride as a solvent). The solid product was isolated and purified by precipitation of its methylene chloride solution into cold 2-propanol. The purified product was isolated by filtration and dried to a constant weight. The composition of CT-2 was determined by IR and MNR; its molecular weight was determined by GPC, and shows to have an $M_n$ of 85 kDa and $M_w$ of 105 kDa. Thermal properties were determined by DSC and indicated a Tm of 159° C. and .DELTA.H.sub.f of 32 J/g.

EXAMPLE 18

Preparation of Acid-terminated Polyglycolide Microparticulates (PG-61)

Glycolide was polymerized in the presence of glycolic acid and stannous octanoate to produce low molecular weight, hydrolytically degradable polyester PG-61, as described in U.S. Pat. No. 6,413,539. Purification and reduction in size of PG-61 was also conducted as per U.S. Pat. No. 6,413,539 teaching.

EXAMPLE 19

Preparation of Dyed, Totally Absorbable Vaginal Ring System and Reinforced with Segmented 88/12 l-Lactide/Trimethylene Carbonate Braided Multifilament (IVR-V): General Method Using the Teflon mold described in Example 4, precharged with 0.5 g of braided multifilament yarn (made of a segmented 88/12 l-lactide trimethylene carbonate copolymer, as described in U.S. Pat. No. 6,342,065, in the form of a circular or ring configuration (with side loops), the matrix components described in table I are mixed and introduced into the mold cavity. The ring curing was conducted for the time periods and the temperatures noted in Table I. At the conclusion of the process, the ring is isolated, processed, coated, and tested as in Example 4.

Components of Individual Type V Rings—The components used in preparing a series of ring system V are described in Table I.

EXAMPLE 20

Preparation of Dyed Totally Absorbable Vaginal Ring Systems having Different pH Modifiers and Reinforced with 95/5 Glycolide/l-Lactide Copolymeric Braided Multifilament (IVR VI)

An IVR type VI was prepared using conditions similar to those used in preparing IVR type V-c (see Table I) with the exception of using a braided multifilament insert made of 95/5 glycolide/l-lactide copolymer.

EXAMPLE 21

Preparation of Dyed Totally Absorbable Vaginal Ring System Reinforced with Braided Multifilament Blends (IVR VII)

A typical ring system, Type VIII, was made under conditions similar to those used in Example 20 with the exception of using a braided multifilament insert comprising 2:1 fiber blend made of 95/5 glycolide/l-lactide and 8812 segmented l-lactide/trimethylene carbonate copolymers at a weight ratio of 2:1, respectively.

EXAMPLE 22

Coating of Ring Systems V to VII with CT-2: General Method

A 5-10 percent solution of CT-2 (from Example 17) in dichloromethane is used for dip-coating representative

TABLE I

Composition of Matrix Components Used in Preparing Individual Type V Intravaginal Rings (IVR) and Curing Conditions

| Matrix Components | Typical Charge for Preparing Two IVR Type V | | | |
|---|---|---|---|---|
| | V-a | V-b | V-c | V-d |
| Components: | | | | |
| Itaconized triaxial 95/5 TMC/G (from Example 16) | ←-------------- 10 g --------------→ | | | |
| Itaconized triaxial 90/10 CL/G (from Example 14) | ←-------------- 4.3 g --------------→ | | | |
| Ferrous Gluconate | ←-------------- 715 mg --------------→ | | | |
| L-Ascorbic Acid | ←-------------- 715 mg --------------→ | | | |
| Acid-terminated PG-61 (from Example 18) | — | 143 mg | — | 858 mg |
| Glycine | — | — | 429 mg | — |
| Lysine | 145 mg | — | — | — |
| 2,2'-Azo-bis-isobutyronitrile | 116 mg | 115 mg | 115 mg | 114 mg |
| Braided multifilament (88/12 LL/TMC) | ←-------------- 150 mg --------------→ | | | |
| D&C Violet #2 | — | ←---- 2 ----→ | | — |
| Curing Conditions | | | | |
| Temperature/Time, ° C./Hour | 80/8 | 80/7 | 80/8 | 80/7 |

Typical Charge for Preparing Two IVR Type V Matrix Components V-a V-b V-c V-d Components: Ferrous Gluconate 715 mg L-Ascorbic Acid 715 mg Glycine - - 429 mg - Lysine 145 mg - - - 116 mg 115 mg 115 mg 114 mg D&C Violet #2 - 2 - Curing Conditions Temperature/Time, .degree. C./Hour 80/8 80/7 80/8 80/7 examples of ring system type V to VII. This ring is dipped using a Teflon hook in the polymer solution for 2 to 10 seconds, depending on the concentration of coating polymer and desired coating add-on. The coated ring is removed from the coating bath and allowed to air-dry for several hours, while being held with a Teflon hook in a laminar flow hood. The drying is then continued at room temperature under reduced pressure until a constant weight is attained.

EXAMPLE 23

Sterilization of Coated and Uncoated Ring Systems V to VII: General Method

In a typical case, the coated or uncoated ring is dipped in absolute 2-propanol for 2 to 10 seconds, depending on the ring type, using a Teflon hook as a holder. The ring is then removed and allowed to dry in a laminar flow hood, while being exposed to UV-C radiation ($\lambda$=240-260 nm) for at least 30 minutes. The ring is then placed in a sterile foil pouch with a Tyvek header. The pouch and its contents were dried under reduced pressure at room temperature to a constant weight. At the conclusion of the drying cycle, the pouch is hermetically sealed.

EXAMPLE 24

Radial Deformation Force (RDF) Measurement for Evaluating Ring Compressibility: General Method The initial compressibility of the ring and percent retention during in vitro degradation was measured in terms of the force (in Newtons) required to deform the ring, radially, by 2.54 cm. The initial compressibility was conducted by placing the ring in the lower component of the sample holder of an MTS Universal Tester (MiniBionix, Model 858) and measuring the force required to deform the upper part of the ring, radially, for a distance of 2.54 cm through the downward movement at a rate of 1 mm/sec, of the free, flat upper component of the sample holder.

To determine the percent retention of ring incubated in a buffered solution at pH 4.5 and 37° C., the test ring was removed at the desired period, wiped with tissue paper to remove excess moisture, and the force of deformation at time "f" (Ft) was measured as noted above for the initial deformation force (Fo) testing. The percent strength retention, in terms of decrease of the RDF, was calculated as follows: % RDF retention=(Fo-Ft÷Fo)×100.

Typical RDF data of a commercial silicone ring (intended for control release of hormones) and representative set of partially and fully absorbable ring system of the present invention are summarized in Table II. Percent retention data of the mechanical properties, in terms of percent RDF for typical IVR are summarized in Table III.

TABLE II

Typical Radial Deformation Force (RDF) Data of Partially and Fully Absorbable Intravaginal Ring (IVR) Systems and a Silicone Control

| Intravaginal Ring Type | RDF, N |
|---|---|
| Silicone Control | 3.29 |
| IVR, Type I (Example 4) | 3.43 |
| Type II (Example 5) | 3.32 |
| Type III (Example 10) | 3.30 |
| Type IV (Example 12) | 3.44 |
| Type V-a (Example 19) | 2.50 |

TABLE II-continued

Typical Radial Deformation Force (RDF) Data of Partially and Fully Absorbable Intravaginal Ring (IVR) Systems and a Silicone Control

| Intravaginal Ring Type | RDF, N |
|---|---|
| Type V-c (Example 19) | 3.0 |
| Type VI (Example 20) | 3.1 |
| Type VII (Example 21) | 3.0 |

TABLE III

Percent Retention Data of the Radial Deformation Force (RDF) of Typical Intravaginal Ring (IVR) Systems

| Ring Type | Initial RDF, N | % RDF Retention @ Day | | | |
|---|---|---|---|---|---|
| | | 2 | 5 | 7 | 14 |
| I | 3.43 | 81 | 50 | — | — |
| II | 3.32 | 100 | 85 | 80 | 60 |
| V-c | 3.0 | 100 | 85 | 80 | 60 |
| VI | 3.1 | 85 | 65 | 50 | 30 |
| VII | 3.0 | 95 | 70 | 60 | 45 |

EXAMPLE 25

Biocompatibility Evaluation

Two experimental protocols (A&B) were used to determine any cytotoxic effect a representative intravaginal ring system (IVR-V) may have on Lactobacillus vaginalis, a desired microorganism of the vaginal flora.

Protocol A: The ring was aseptically cut into 1/4" sections and placed in culture tubes containing 10 mL of MRS broth inoculated with an overnight culture of L. vaginalis. The tubes were grown at 37° C. with 5% $CO_2$ for 14 hours. The growth of the L. vaginalis was determined by measuring the OD of the cultures on a spectrophotometer.

Protocol B: Other 1/4" sections of the ring were placed into culture tubes containing 10 mL of phosphate buffer, pH 4.5. These tubes were incubated at 37° C. At days 1, 2, 3, 7, and 10 the eluant was added to MRS broth inoculated with L. vaginalis. The following concentrations of eluant 1%, 5%, 10%, and 50% were tested. The tubes were incubated as above and OD measurements taken to determine growth.

The results revealed the cytocompatibility of the solid ring components. Protocol A showed no adverse affect to the growth of the L. vaginalis when the intact ring was added to the culture. Protocol B demonstrated that components of the ring or their degradation products, which might be present in the eluant, were also compatible with L. vaginalis growth.

EXAMPLE 26

Determination of Daily and Cumulative In Vitro Release Rates of Ferrous Gluconate from Eluates of a Typical Spermiostatic Ring System Outline of the Experimental Procedure The procedure consists of: (1) cutting pieces of a typical ring system (as in Examples 10, 12, 19, 20, and 21) and recording the weight (pieces are placed in separate, labelled Petri dishes); (2) placing the pieces of the ring containing ferrous gluconate into a shaker containing 5 mL of phosphate buffered saline or water to Petri dishes, sealing with parafilm, and incubating at 37° C. overnight; (3) collecting the eluate and measuring the volume each day, then transferring the ring pieces to a new Petri plate in 5 mL of fresh phosphate buffered saline and following Step (2) above; (4) continuing the above procedure daily for 2-days, then drying the residual matrix and recording the final weight; (5) determining the amount of ferrous gluconate in each daily collection of the eluate; (6) testing an aliquot from each eluate to determine the spermiostatic activity (by semen analysis); and (7) recording the pH of the eluates (water is used as a solvent when testing for pH).

Determination of Cumulative Release Rates of Iron from Eluates

The rates are determined in the following manner: (1) cutting pieces of the ring and placing them in a Petri dish and recording the weight; (2) adding 5 mL of PBS or water to the dish; (3) collecting 1 mL of the eluate from the Petri dish daily and replenishing with fresh PBS or water to make up the final volume to 5 mL; and (4) determining ferrous gluconate content in the aliquot collected and testing an aliquot for spermiostatic activity.

EXAMPLE 27

Determination of Ferrous Gluconate by the 1,10 Phenanthroline Method

Phenanthroline forms an orange-red colored complex with the ferrous ion, which is analyzed spectrophotometrically. The color is stable for days. Hydroquinone reduces any ferric iron that may have been formed due to oxidation of ferrous exposed to the environment. All solutions used are maintained at a pH of 3.5.

Reagents used included (1) stock solution of 10.times. phosphate buffered saline (PBS); (2) 1% solution of hydroquinone; (3) 0.5% solution of 1,10-phenanthroline (is kept in dark and discarded if any color develops); (4) sodium acetate-acetate acid buffer solution of pH 4 (is prepared by dissolving 27 grams of anhydrous sodium acetate in 50 mL of distilled water and adding 24 mL of acetic acid and dilute to 100 mL); (5) ferrous gluconate (50.0 mm) (is prepared by dissolving 0.224 g I 20 mL PBSO; and bromophenol blue dye indicator (pH range 3.0-4.6).

Procedure: From each of the unknown solutions or samples, 500 .mu.L (containing approximately 0.01-0.02 mg ferrous gluconate) are transferred to 5 mL test tubes. For the standard, a 0.5 mM ferrous gluconate solution is prepared in PBS in serial dilutions. A 600 .mu.L aliquot is taken from each of the known serial dilutions of the standard solution and transferred to 5 mL test tubes. Using a micropipette, one drop of bromophenol blue is added to the test tubes followed by one drop of sodium acetate. To each tube of the standard solution and each of the unknown solutions, 1 mL of 1% hydroquinone is added and followed by 1 mL of 0.5% 1,10-phenanthroline. Each tube is Vortexed gently. The mixture is allowed to stand for one hour or longer at room temperature. Transmittance at 408 nm was measured using a spectrophotometer. Values derived from standard solutions of ferrous gluconate were plotted. From the absorbance curve, the concentration of ferrous gluconate in the eluates is then determined.

EXAMPLE 28

Determination of L-Ascorbic Acid

In this procedure, ascorbic acid is oxidized to dehydroascorbic acid and the latter is coupled with 2,4-dinitrophenylhydrazine. The coupling reaction forms the 2,4-dinitrophnylosazone of dehydroascorbic acid, a light brown crystalline compound. When treated with 85% H.sub.2SO.sub.4, the osazone is rearranged to form a reddish colored compound, which absorbs maximally at 500 to 550 .mu.m. It is a highly stable product under the conditions used and was well suited to colorimetric measurement.

Preparation of Reagents:

Reagents used included (1) trichloroacetic acid solutions, 6% and 4%; (2) 2,4-dinitrophenylhydrazine reagent (2.0 g of 2,4-dinitrophenylhydrazine were dissolved in 100 mL 9N H.sub.2SO.sub.4 [1 part of concentrated H.sub.2SO.sub.4 plus 3 parts water], 4 g of reagent thiourea were added, shaken occasionally, dissolved, filtered and then refrigerated; and (3) ascorbic acid solutions.

Stock Solution: Ascorbic acid of the highest purity (50 mg) is dissolved in 100 mL of 0.5% oxalic acid. Keep refrigerated.

Standard Solution of Dehydroascorbic Acid: Two mL of the ascorbic acid stock solution are placed in a 100-mL volumetric flask and make up to volume with 4% trichloroacetic acid solution. This solution is oxidized by adding one teaspoon (or 1 g) of acid-washed Norite per 50 mL, shaking thoroughly, and filtering through Whatman No. 42 filter paper. One mL of this solution contains 10 .mu.g of dehydroascorbic acid. Keep refrigerated.

Preparation of Solution Filtrate: To one volume of solution, add 10 volumes of 4.0% trichloroacetic acid are added. This dilution will serve for a range of 1 to 300 mg of ascorbic acid per liter of solution.

Procedure: Four mL of Norite filtrate of unknowns are placed in each of two matched photoelectric colorimeter tubes. In another matched colorimeter tube are placed 4 mL of the dehydroascrobic acid standard solution (10 .mu.g per mL). To the standard tube and the tube containing Norite filtrate, add 1.0 mL of 2,4-dinitrophenylhydrazine reagent. The other tube containing Norite filtrate is used as a control, no reagent being added to the tube at this time. The three tubes are placed in a constant temperature water bath at 37° C. The tubes are kept immersed in the bath for exactly 3 hours, removed, and subsequently placed in a beaker of ice water containing generous quantities of ice. To each of the three tubes in the ice water bath is added slowly 5.0 mL of 85% H.sub.2SO.sub.4. Finally, to the control and experimental tubes, 1 mL 2,4-dinitrophenylhydrazine reagent is added and tubes are shaken under the ice water to obtain complete mixing and are then removed to a rack. After 30 minutes, the tubes are wiped and cleaned to record the absorption in a calorimeter, using 540 m.mu. filter. To take the reading, the control tube is used to set the colorimeter at 100% transmittance or zero absorbance.

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. A composite ring system for release of at least one bioactive agent at a specified biological site comprising:
   a microporous matrix;
   a polymer selected from the group consisting of polyesters, polyamides, polyurethanes, polyorthoesters, and polyanhydrides, or combinations of the above;
   at least one bioactive agent;
   wherein the composite ring system has at least two modes of controlling the release of the at least one bioactive agent; and
   wherein the composite ring system is fully absorbable.

2. The composite ring system of claim 1, further comprising a polymeric outer coating.

3. The composite ring system of claim 2, wherein the polymeric outer coating modulates release of the bioactive agents.

4. The composite ring system of claim 2, wherein the polymeric outer coating comprises a bioadhesive.

5. The composite ring system of claim 1, wherein the at least one bioactive agent is released over a period of time ranging from one day to six months.

6. The composite ring system of claim 1, wherein the microporous matrix comprises at least two different polymers.

7. The composite ring system of claim 6, wherein the microporous matrix comprises a polyurethane selected from the group consisting of polyesters, polyether-esters, and polyether-ester-urethanes, or combinations thereof.

8. The composite ring system of claim 6, wherein the microporous matrix comprises a naturally derived polymers such as chitosan, alginate, casein or collagen.

9. The composite ring system of claim 1, further comprising a reinforcing fiber made of an absorbable/biodegradable polymer.

10. The composite ring system of claim 9, wherein the reinforcing fiber exhibits a strength retention profile to control decrease in mechanical properties and resilience of the ring system over time.

11. The composite ring system of claim 9, wherein the reinforcing fiber comprises a multifilament or monofilament yarn.

12. The composite ring system of claim 11, wherein the at least one bioactive agent comprises an infertility agent, antimicrobial agent, antiviral agent, oncologic agent, or combinations of the above.

13. The composite ring system of claim 1, wherein the matrix has a linear structure.

14. The composite ring system of claim 1, wherein the at least one bioactive agent is selected from the group comprising a contraception agent, labor induction agent, antibacterial agent, antifungal agent, antiviral agent, antiparasitic agent, cervical cancer agent, or ovarian cancer agent, or combinations of the above.

15. The composite ring system of claim 1, wherein the at least one bioactive agent is selected from the group comprising a spermiostatic, spermicidal, hormonal agent or viscosity modifier.

16. The composite of claim 1, wherein the composite has three modes of controlling release of the at least one bioactive agents.

17. A composite ring system for release of at least one bioactive agent at a specified biological site comprising:
   the composite ring system comprising absorbable and nonabsorbable components;
   a matrix;
   wherein the matrix comprises linear or cross-linked chain molecules;
   a polymer comprising dispersed sequences selected from the group consisting of ester, ether, urethane, and peptide, or combinations of the above;
   at least one bioactive agent; and
   wherein the composite ring system has at least two modes of controlling the release of the at least one bioactive agent.

18. The composite ring system of claim 17, wherein the matrix becomes microporous after introduction to the biological site.

19. The composite ring system of claim 17, wherein the matrix comprises absorbable and nonabsorbable components.

20. The composite ring system of claim 17, wherein the matrix is nonabsorbable and comprises either polydimethylsiloxane or a methacrylate polymer.

21. The composite ring system of claim 18, wherein the matrix is nonabsorbable, comprises the methacrylate polymer which further comprises repeat units derived from one or more alkylmethacrylates and optionally either vinyl acetate or N-vinyl pyrrolidone.

22. The composite ring system of claim 18, wherein the microporous matrix comprises polydimethylsiloxane.

23. The composite ring system of claim 17, wherein the matrix is fully absorbable.

24. The composite ring system of claim 17, wherein the matrix comprises synthetic polymers, naturally derived polymers, or combinations of the above.

25. The composite ring system of claim 24, wherein the synthetic polymers are selected from the group consisting of polyesters, polyether-esters, polyether-ester-urethanes, or combinations of the above.

26. The composite ring system of claim 24, wherein the naturally derived polymers are selected from the group consisting of chitosan, alginate, casein, collagen, or combinations of the above.

27. The composite ring system of claim 24, wherein the matrix comprises a combination of a synthetic and a naturally derived polymer further comprising cyclodextrin or cyclodextrin derivatives.

28. The composite ring system of claim 17, wherein the at least one bioactive agent comprises an infertility agent, antimicrobial agent, antiviral agent, oncologic agent, or combinations of the above.

29. A composite ring system for release of at least one bioactive agent at specified biological site comprising:
   a matrix;
   a fibrous reinforcing construct;
   an absorbable coating;
   a polymer selected from the group consisting of polyesters, polyamides, polyurethanes, polyorthoesters, and polyanhydrides, or combinations of the above;
   and at least one bioactive agent;
   wherein the composite ring system has at least two modes of controlling the release of the at least one bioactive agent; and
   wherein the composite ring system is fully absorbable.

30. The composite ring system of claim 29, wherein release of the at least one bioactive agent is controlled by the matrix, the fibrous reinforcing construct, the absorbable coating, or combinations of the above.

31. The composite ring system of claim 29, wherein the at least one bioactive agent comprises an infertility agent, antimicrobial agent, antiviral agent, oncologic agent, or combinations of the above.

32. The composite ring system of claim 29, wherein the matrix is microporous.

33. The composite ring system of claim 29, wherein the matrix is not microporous.

34. The composite ring system of claim 29, wherein the matrix further comprises a water-soluble excipient to facilitate release of the at least one bioactive agent.

35. The composite ring system of claim 29, wherein the fibrous reinforcing construct comprises a twisted yarn, braid, twisted/coated staples, or non-woven fabric in the form of a ring structure.

36. The composite ring system of claim 1, further comprising a mode of release control other than simple diffusion or physical liberation as the matrix degrades.

\* \* \* \* \*